US011821004B2

(12) United States Patent
Danilkovitch et al.

(10) Patent No.: US 11,821,004 B2
(45) Date of Patent: Nov. 21, 2023

(54) MESENCHYMAL STEM CELLS EXPRESSING TNF-α RECEPTORS

(71) Applicant: Mesoblast International Sárl, Meyrin (CH)

(72) Inventors: Alla Danilkovitch, Columbia, MD (US); Diane Carter, Huntington, MD (US); Alicia Mildred Tyrell, Cantonsville, MD (US); Simon Bubnic, Ann Arbor, MI (US); Michelle Marcelino, IJamsville, MD (US); Rodney Monroy, Aberdeen, MD (US)

(73) Assignee: MESOBLAST INTERNATIONAL SÁRL, Meryin (CH)

( * ) Notice: Subject to any disclaimer, the term of this patent is extended or adjusted under 35 U.S.C. 154(b) by 252 days.

(21) Appl. No.: 17/087,124

(22) Filed: Nov. 2, 2020

(65) Prior Publication Data
US 2021/0171913 A1  Jun. 10, 2021

Related U.S. Application Data (60) Continuation of application No. 15/693,754, filed on Sep. 1, 2017, now abandoned, which is a continuation of application No. 14/228,327, filed on Mar. 28, 2014, now abandoned, which is a continuation of application No. 13/906,592, filed on May 31, 2013, now abandoned, which is a division of application No. 13/402,498, filed on Feb. 22, 2012, now Pat. No. 8,486,695, which is a continuation of application No. 12/091,391, filed as application No. PCT/US2007/000274 on Jan. 5, 2007, now abandoned.

(60) Provisional application No. 60/759,157, filed on Jan. 13, 2006.

(51) Int. Cl.
| | |
|---|---|
| *A01N 63/00* | (2020.01) |
| *G01N 33/53* | (2006.01) |
| *C12N 5/00* | (2006.01) |
| *C12N 5/0775* | (2010.01) |
| *A61K 35/28* | (2015.01) |
| *A01K 67/00* | (2006.01) |
| *A61K 35/12* | (2015.01) |

(52) U.S. Cl.
CPC ............ *C12N 5/0662* (2013.01); *A61K 35/28* (2013.01); *C12N 5/0663* (2013.01); *A61K 2035/122* (2013.01); *C12N 2501/25* (2013.01); *G01N 2333/525* (2013.01)

(58) Field of Classification Search
CPC ............... C12N 5/0662; C12N 5/0663; C12N 2501/25; A61K 35/28; A61K 2035/122; G01N 2333/525

See application file for complete search history.

(56) References Cited

U.S. PATENT DOCUMENTS

| | | |
|---|---|---|
| 5,486,359 A | 1/1996 | Caplan et al. |
| 5,955,257 A | 9/1999 | Burger et al. |
| 6,007,995 A | 12/1999 | Baker et al. |
| 6,071,889 A | 6/2000 | Weiss et al. |
| 6,225,119 B1 | 5/2001 | Qasba et al. |
| 6,251,295 B1 | 6/2001 | Johnson |
| 6,328,960 B1 | 12/2001 | McIntosh et al. |
| 6,368,636 B1 | 4/2002 | McIntosh et al. |
| 6,797,269 B2 | 9/2004 | Mosca et al. |
| 6,797,514 B2 | 9/2004 | Berenson et al. |
| 6,875,430 B2 | 4/2005 | McIntosh et al. |
| 6,974,571 B2 | 12/2005 | Prockop et al. |
| 7,037,492 B2 | 5/2006 | Glorioso et al. |
| 8,105,580 B2 | 1/2012 | Fraser et al. |
| 8,147,824 B2 | 4/2012 | Mazairz et al. |
| 8,404,229 B2 | 3/2013 | Fraser et al. |
| 8,440,177 B2 | 5/2013 | González De La Pena et al. |
| 8,486,695 B2 | 7/2013 | Danilkovitch et al. |
| 8,637,004 B2 | 1/2014 | Danilkovitch et al. |
| 9,694,035 B2 | 7/2017 | Aggarwal et al. |
| 9,828,586 B2 | 11/2017 | Tom et al. |
| 9,943,547 B2 | 4/2018 | Aggarwal et al. |
| 9,963,678 B2 | 5/2018 | Tom et al. |
| 10,550,369 B2 | 2/2020 | Tom et al. |
| 10,668,101 B2 | 6/2020 | Aggarwal et al. |
| 10,716,814 B2 | 7/2020 | Aggarwal et al. |
| 10,729,727 B2 | 8/2020 | Aggarwal et al. |
| 10,828,334 B1 | 11/2020 | Aggarwal et al. |
| 10,960,025 B2 | 3/2021 | Aggarwal et al. |
| 11,389,484 B2 | 7/2022 | Aggarwal et al. |

(Continued)

FOREIGN PATENT DOCUMENTS

| | | |
|---|---|---|
| JP | H10501815 A | 2/1998 |
| JP | 2002510655 A | 4/2002 |

(Continued)

OTHER PUBLICATIONS

Griffin et al. Anti-donor immune responses elicited by allogeneic mesenchymal stem cells: what have we learned so far? Immunology and Cell Biology 91:40-51, (Year: 2013).*

Jorgensen, C., et al., "Mesenchymal stem cells and rheumatoid arthritis," *Joint Bone Spine* 70(6):483-485, Elsevier, Netherlands (Dec. 2003).

El-Badri, N. S., et al., "Mesenchymal stem cells in autoimmune disease," *Stem Cells Dev* 13(5):463-472, Mary Ann Liebert Inc., United States (Oct. 2004).

(Continued)

*Primary Examiner* — Quang Nguyen
(74) *Attorney, Agent, or Firm* — Sterne, Kessler, Goldstein & Fox P.L.L.C.

(57) ABSTRACT

Mesenchymal stem cells which express TNF-α receptor Type I in an amount of at least 13 pg/10⁶ cells. Such mesenchymal stem cells inhibit the proliferation of lymphocytes and may be employed, in particular, in the treatment of graft-versus-host disease.

13 Claims, 2 Drawing Sheets

(56) References Cited

U.S. PATENT DOCUMENTS

| | | |
|---|---|---|
| 11,491,188 B2 | 11/2022 | Itescu et al. |
| 2002/0044923 A1 | 4/2002 | Mosca et al. |
| 2003/0165482 A1 | 9/2003 | Rolland et al. |
| 2004/0033214 A1 | 2/2004 | Young et al. |
| 2004/0241141 A1 | 12/2004 | Pawliuk et al. |
| 2005/0239897 A1 | 10/2005 | Pittenger et al. |
| 2006/0063141 A1 | 3/2006 | McGann et al. |
| 2006/0110825 A1 | 5/2006 | Alessandri et al. |
| 2006/0134596 A1 | 6/2006 | Sjogren et al. |
| 2007/0258963 A1 | 11/2007 | Danilkovitch et al. |
| 2014/0161776 A1 | 6/2014 | Aggarwal et al. |
| 2018/0087032 A1 | 3/2018 | Danilkovitch et al. |
| 2019/0175657 A1 | 6/2019 | Aggarwal et al. |
| 2019/0201447 A1 | 7/2019 | Aggarwal et al. |
| 2019/0240259 A1 | 8/2019 | Aggarwal et al. |
| 2020/0197444 A1 | 6/2020 | Danilkovitch et al. |
| 2020/0231936 A1 | 7/2020 | Tom et al. |
| 2020/0246387 A1 | 8/2020 | Aggarwal et al. |
| 2021/0163932 A1 | 6/2021 | Brink et al. |
| 2022/0079991 A1 | 3/2022 | Itescu |
| 2022/0143097 A1 | 5/2022 | Itescu et al. |
| 2022/0160776 A1 | 5/2022 | Itescu et al. |
| 2022/0226386 A1 | 7/2022 | Itescu |
| 2022/0275337 A1 | 9/2022 | Devine et al. |
| 2023/0076630 A1 | 3/2023 | Aggarwal et al. |
| 2023/0089901 A1 | 3/2023 | Danilkovitch et al. |
| 2023/0097931 A1 | 3/2023 | Itescu |
| 2023/0104108 A1 | 4/2023 | Itescu |

FOREIGN PATENT DOCUMENTS

| | | |
|---|---|---|
| WO | WO-9534320 A2 | 12/1995 |
| WO | WO-0104268 A1 | 1/2001 |
| WO | WO 2005/093044 A1 | 10/2006 |
| WO | WO 2007/084354 A2 | 7/2007 |
| WO | WO-2007123363 A1 | 11/2007 |
| WO | WO 2008/042174 A2 | 4/2008 |
| WO | WO 2008/116157 A2 | 9/2008 |

OTHER PUBLICATIONS

Aggarwal et al., "Human mesenchymal stem cells modulate allogeneic immune cell responses," Blood 105:1815-1822 (2005).

Ballas et al., "Adult bone marrow stem cells for cell and gene therapies: implications for greater use," J. Cell. Biochem. Suppl., 38:20-28 (2002).

Chopp et al., "Spinal cord injury in rat: treatment with bone marrow stromal cell transplantation," Neuroreport, 11:3001-3005 (2000).

Czitrom, "The immune response: the afferent arm," Clin. Orthop. Relat. Res., 326:11-24 (1996).

Deans et al., "Mesenchymal stem cells: biology and potential clinical uses," Exp. Hematol., 28:875-884 (2000).

Debets et al., "Expression of cytokines and their receptors by psoriatic fibroblasts. II. decreased TNF receptor expression," Cytokine, 8:80-88 (1996).

DeKok et al., "Investigation of allogeneic mesenchymal stem cell-based alveolar bone formation: preliminary findings" Clin. Oral Implants Res., 14:481-489 (2003).

Di Nicola et al., "Human bone marrow stromal cells suppress T-lymphocyte proliferation induced by cellular or nonspecific mitogenic stimuli," Blood, 99:3838-3843 (2002).

Eaves et al., "Characterization of human hematopoietic cells with short-lived in vivo repopulating activity," Ann. NY Acad. Sci., 938:63-70 (2001).

Ellison et al., "Effect of recombinant human keratinocyte growth factor (rHuKGF) on the immunopathogenesis of intestinal graft-vs.-host disease induced without a preconditioning regimen," J. Clin. Immunol., 24:197-211 (2004).

European Search Report in EP 07716359.0-2401, dated Nov. 5, 2009.

Foster et al., "Long-term acceptance of composite tissue allografts through mixed chimerism and CD28 blockade," Transplantation, 76(6):988-994 (2003).

Frassoni et al., Int. Society for Cell Therapy, SA 006 (abstract) (2002).

Fukuda, "Development of regenerative cardiomyocytes from mesenchymal stem cells for cardiovascular tissue engineering," Artif. Organs, 25:187-193 (2001).

Gerstenfeld et al., "Impaired intramembranous bone formation during bone repair in the absence of tumor necrosis factor-alpha signaling," Cells Tissues Organs, 169:285-294 (2001).

Haynesworth et al., "Cell surface antigens on human marrow-derived mesenchymal cells are detected by monoclonal antibodies," Bone, 13:69-80 (1992).

Horwitz et al., "Clinical responses to bone marrow transplantation in children with severe osteogenesis imperfecta," Blood, 97:1227 (2001).

Horwitz et al., "Isolated allogeneic bone marrow-derived mesenchymal cells engraft and stimulate growth in children with osteogenesis imperfecta: Implications for cell therapy of bone," Proc. Natl. Acad. Sci. USA, 99:8932-8937 (2002).

International Search Report in International Patent Application No. PCT/US07/00274, dated Jul. 18, 2007.

Koc et al., "Rapid hematopoietic recovery after coinfusion of autologous-blood stem cells and culture-expanded marrow mesenchymal stem cells in advanced breast cancer patients receiving high-dose chemotherapy," J. Clin Oncol., 18:307-316 (2000).

Koide et al., "Increased expression of tissue cytokines in graft-versus-host disease after small bowel transplantation in the rat," Transplantation, 64:518-524 (1997).

Koulova et al., "The CD28 ligand B7-BB1 provides costimulatory signal for alloactivation of CD4+ T cells," J. Exp. Med., 173(3):759-762 (1991).

Kuroiwa et al., "Hepatocyte gowth factor ameliorates acute graft-versus-host disease and promotes hematopoietic function," J. Clin. Invest., 107:1365-1373 (2001).

Le Blanc et al., "Treatment of severe acute graft-versus-host disease with third party haploidentical mesenchymal stem cells," The Lancet., 363:1439-1441 (2004).

Mackenzie et al., "Human mesenchymal stem cells persist, demonstrate site-specific multipotential differentiation, and are present in sites of would healing and tissue regeneration after transplantation into fetal sheep," Blood Cells Mol. Dis., 27:601-604 (2001).

Noel et al., "Regenerative medicine through mesenchymal stem cells for bone and cartilage repair," Curr. Opin. Investig. Drugs, 3:1000-1004 (2002).

Final Office Action dated Nov. 17, 2008, in U.S. Appl. No. 11/650,374, filed Jan. 5, 2007.

Non-Final Office Action dated Jun. 17, 2008, in U.S. Appl. No. 11/650,374, filed Jan. 5, 2007.

Advisory Action dated Jan. 28, 2009, in U.S. Appl. No. 11/650,374, filed Jan. 5, 2007.

Non-Final Office Action dated Dec. 8, 2010, in U.S. Appl. No. 12/091,391, filed Sep. 15, 2008.

Non-Final Office Action dated Jan. 25, 2011, in U.S. Appl. No. 12/091,391, filed Sep. 15, 2008

Final Office Action dated Oct. 3, 2011, in U.S. Appl. No. 12/091,391, filed Sep. 15, 2008.

Ojwang et al., "Modified antisense oligonucleotides directed against tumor necrosis factor receptor type I inhibit tumor necrosis factor alpha-mediated functions," Biochemistry, 36L6033-6045 (1997).

Pereira et al., "Marrow stromal cells as a source of progenitor cells for nonhematopoietic tissues in transgenic mice with a phenotype of osteo genesis imperfecta," Proc. Natl. Acad. Sci. USA, 95:1142-1147 (1998).

Pittenger et al., "Multilineage potential of adult human mesenchymal stem cells," Science, 284:143 (1999).

Prockop, "Multipotency of a bone marrow stromal cell line, TBR31-2, established from ts-SV40 T antigen gene transgenic mice," Science, 276-71-74 (1997).

Sanchez-Ramos et al., "Expression of neural markers in human umbilical cord blood," Exp. Neurol., 171:109-115 (2001).

(56) References Cited

OTHER PUBLICATIONS

Schwartz et al., "Multipotential marrow stromal cells transduced to produce L-DOPA: engraftment in a rat model of Parkinson disease," Hum. Gene Ther., 10:2539 (1999).
Shake et al., "Mesenchymal stem cell implantation in a swine myocardial infarct model: engraftment and functional effects," Ann. Thorac. Surg., 73:1919-1925 (2002).
Shen et al., "Inhibition of p75 tumor necrosis factor receptor by antisense oligonucleotides increases hypoxic injury and beta-amyloid toxicity in human neuronal cell line," J. Biol. Chem., 272:3550-3553 (1997).
Tartaglia et al., "The two different receptors for tumor necrosis factor mediate distinct cellular responses," Proc. Natl. Acad. Sci. USA, 88:9292-9296 (1991).
Toma et al., "Human mesenchymal stem cells differentiate to a cardiomyocyte phenotype in the adult murine heart," Circulation, 105:93-98 (2002).
Tomita et al., "Autologous transplantation of bone marrow cells improves damages heart function," Circulation, 100:247-256 (1999).
Trickett et al., "T cell stimulation and expansion using anti-CD3/CD28 beads," J. Immunol. Methods, 275:251-255 (2003).
Tse et al., "Suppression of allogeneic T-cell proliferation by human marrow stromal cells: implications in transplantation," Transplantation, 75:389-397 (2003).
Vancheri et al., "Different Expression of TNF—α Receptors and Prostaglandin $E_2$Production in Normal and Fibrotic Lung Fibroblasts," Am. J. Respir. Cell Mol. Biol., 22:628-634 (2000).
Wagers et al., "Cell fate determination from stem cells," Gene Ther., 9:606-612 (2002).
Wakitani et al., "Myogenic cells derived from rat bone marrow mesenchymal stem cells exposed to 5-azacytidine," Muscle Nerve, 18:1417-1426 (1995).
Woodbury et al., "Adult bone marrow stromal cells express germline, ectodermal, endodermal, and mesodermal genes prior to neurogenesis," J. Neurosci. Res., 69:908-917 (2002).
Written Opinion of the International Searching Authority in International Patent Application No. PCT/US07/00274, dated Jul. 18, 2007.
Non-Final Office Action dated Jul. 11, 201, in U.S. Appl. No. 13/085,720, filed Apr. 13, 2011.
Barbet, R., et al., "Comparison of Gene Expression in Human Embryonic Stem Cells, hESC-Derived Mesenchymal Stem Cells and Human Mesenchymal Stem Cells," Stem Cells Int. 2011:368192 (2011).
Wu et al., "Migration of mesenchymal stem cells to heart allografts during chronic rejection," Transplantation, 75:679-685 (2003).
Wu et al., "Bone marrow stromal cells enhance differentiation of cocultured neurosphere cells and promote regeneration of injured spinal cord," J. Neurosci, Res., 72:393-404 (2003).
Bilic, G. et al., "In vitro lesion repair by human amnion epithelial and mesenchymal cells", Amer. Journal of Obstetrics and Gynecology, vol. 190, No. 1, Jan. 2004 (Jan. 2004), pp. 87-92, XP009164009.
Tarte, J. et al., "INF-Gamma, Unlike TNF-Alpha, LPS, or CD40 Signal, is Required and Sufficient to Induce Indoleamine 2,3-Dioxygenase Activity in Mesenchymal Stem Cells," Blood, Amer. Society Hematology, US, vol. 106, No. 11, (2005), pp. 650A, XP008080026.
Eggenhofer et al. "Rat mesenchymal stromal cells inhibit T cell proliferation but not cytokine production through inducible nitric oxide synthase," Frontiers in Immunology 3:1-8, 2012.

Non-Final Office Action dated Jul. 13, 2015, in U.S. Appl. No. 14/484,444, filed Sep. 12, 2014.
Final Office Action dated Mar. 29, 2016, in U.S. Appl. No. 14/484,444, filed Sep. 12, 2014.
Non-Final Office Action dated Dec. 23, 2016 in U.S. Appl. No. 14/484,444, filed Sep. 12, 2014.
Non-Final Office Action dated Jun. 10, 2014, in U.S. Appl. No. 14/228,327, filed Mar. 28, 2014.
Final Office Action dated Nov. 4, 2014, in U.S. Appl. No. 14/228,327, filed Mar. 28, 2014.
Non-Final Office Action dated Feb. 27, 2015, in U.S. Appl. No. 14/228,327, filed Mar. 28, 2014.
Final Office Action dated Jul. 8, 2015, in U.S. Appl. No. 14/228,327, filed Mar. 28, 2014.
Le Blanc et al. "Treatment of Severe Acute Graft-Versus-Host Disease With Third Party Haploidentical Mesenchymal Stem Cells," The Lancet, vol. 363, pp. 1439-1441 (2004).
Co-pending, U.S. Appl. No. 16/815,784, inventors Aggarwal, S., et al., filed Mar. 11, 2020 (Not Published).
Mohiuddin, M., "Clinical Xenotransplantation of Organs: Why Aren't We There Yet?" PLoS Medicine 4:0429-0434 (Mar. 2007).
Miao, D., et al., "Megakaryocyte-bone marrow stromal cell aggregates demonstrate increased colony formation and alkaline phosphatase expression in vitro," Tissue Eng. 10(5-6):807-817, Mary Ann Liebert, Inc., United States (2004).
Kasakura, S., "[A role for T-helper type 1 and type 2 cytokines in the pathogenesis of various human diseases]," Rinsho Byori: The Japanese Journal of Clinical Pathology 46(9):915-921, Nihon Rinsho Byori Gakkai, Japan (1998).
Kosuge, T., et al., "[Effects of psidium components on cytokine productions in helper T cells and type-I allergy]," Yakugaku Zasshi (Journal of the Pharmaceutical Society of Japan) 120(4):408-412, Pharmaceutical Society of Japan, Japan (2000).
Takeba, Y., "[Functions and expression of Txk, a non-receptor tyrosine kinase of the Tec family]," BioMed Central, United Kingdom (2003).
Meisel, R., et al., "Human bone marrow stromal cells inhibit allogeneic T-cell responses by indoleamine 2,3-dioxygenase-mediated tryptophan degradation," Blood 103(12):4619-4621, American Society of Hematology, United States (2004).
Ortiz, L.A., et al., "Mesenchymal stem cell engraftment in lung is enhanced in response to bleomycin exposure and ameliorates its fibrotic effects," Proc. Natl. Acad. Sci. USA 100:8407-8411, National Academy of Sciences, United States (2003).
Dahl, J.A., et al., "Genetic and Epigenetic Instability of Human Bone Marrow Mesenchymal Stem Cells Expanded in Autologous Serum or Fetal Bovine Serum," The International Journal of Developmental Biology 52(8):1033-1042, University of the Basque Country Press, Spain (2008).
Co-pending U.S. Appl. No. 17/905,742, inventor Itescu, S., filed Sep. 6, 2022 (Not Published).
Co-pending U.S. Appl. No. 17/906,160, inventor Itescu, S., filed Sep. 12, 2022 (Not Published).
Co-pending U.S. Appl. No. 17/995,385, inventor Itescu, S., filed Oct. 3, 2022 (Not Published).
Co-pending U.S. Appl. No. 18/001,462, inventor Simmons, P., et al., filed Dec. 9, 2022 (Not Published).
Co-pending U.S. Appl. No. 18/041,330, inventor Itescu, S., et al., filed Feb. 10, 2023 (Not Published).
Co-pending U.S. Appl. No. 18/041,303, inventor Itescu, S., et al., filed Feb. 10, 2023 (Not Published).

* cited by examiner

MESENCHYMAL STEM CELLS EXPRESSING TNF-α RECEPTORS

RELATED APPLICATIONS

This application is a continuation of U.S. patent application Ser. No. 15/693,754, filed on Sep. 1, 2017, which is a continuation of U.S. patent application Ser. No. 14/228,327, filed on Mar. 28, 2014, which is a continuation of U.S. patent application Ser. No. 13/906,592, filed on May 31, 2013, which is a divisional of U.S. patent application Ser. No. 13/402,498, filed on Feb. 22, 2012, now U.S. Pat. No. 8,486,695, which is a continuation of U.S. patent application Ser. No. 12/091,391, filed on Sep. 15, 2008, which is a National Stage Entry of international patent application number PCT/US07/00274, filed on Jan. 5, 2007, which claims priority to U.S. Provisional Patent Application Ser. No. 60/759,157, filed on Jan. 13, 2006; the contents of all of which are hereby incorporated by reference in their entireties.

BRIEF SUMMARY OF THE INVENTION

This invention relates to mesenchymal stem cells. More particularly, this invention relates to mesenchymal stem cells which express tumor necrosis factor-alpha (TNF-α) receptors, and in particular, the tumor necrosis factor-alpha (TNF-α) receptor Type I (TNFRI), in an amount of at least 13 pg/$10^6$ cells. Such mesenchymal stem cells inhibit lymphocyte proliferation.

Mesenchymal stem cells (MSCs) are multipotent stem cells that can differentiate readily into lineages including osteoblasts, myocytes, chondrocytes, and adipocytes (Pittenger, et al., *Science*, Vol. 284, pg. 143 (1999); Haynesworth, et al., *Bone*, Vol. 13, pg. 69 (1992); Prockop, *Science*, Vol. 276, pg. 71 (1997)). In vitro studies have demonstrated the capability of MSCs to differentiate into muscle (Wakitani, et al., *Muscle Nerve*, Vol. 18, pg. 1417 (1995)), neuronal-like precursors (Woodbury, et al., *J. Neurosci. Res.*, Vol. 69, pg. 908 (2002); Sanchez-Ramos, et al., *Exp. Neurol.*, Vol. 171, pg. 109 (2001)), cardiomyocytes (Toma, et al., *Circulation*, Vol. 105, pg. 93 (2002); Fakuda, *Artif. Organs*, Vol. 25, pg. 187 (2001)) and possibly other cell types. In addition, MSCs have been shown to provide effective feeder layers for expansion of hematopoietic stem cells (Eaves, et al., *Ann. N.Y. Acad. Sci.*, Vol. 938, pg. 63 (2001); Wagers, et al., *Gene Therapy*, Vol. 9, pg. 606 (2002)).

Recent studies with a variety of animal models have shown that MSCs may be useful in the repair or regeneration of damaged bone, cartilage, meniscus or myocardial tissues (DeKok, et al., *Clin. Oral Implants Res.*, Vol. 14, pg. 481 (2003)); Wu, et al., *Transplantation*, Vol. 75, pg. 679 (2003); Noel, et al., *Curr. Opin. Investig. Drugs*, Vol. 3, pg. 1000 (2002); Ballas, et al., *J. Cell. Biochem. Suppl.*, Vol. 38, pg. 20 (2002); Mackenzie, et al., *Blood Cells Mol. Dis.*, Vol. 27, pgs. 601-604 (2001)). Several investigators have used MSCs with encouraging results for transplantation in animal disease models including osteogenesis imperfecta (Pereira, et al., *Proc. Nat. Acad. Sci.*, Vol, 95, pg. 1142 (1998)), parkinsonism (Schwartz, et al., *Hum. Gene Ther.*, Vol. 10, pg. 2539 (1999)), spinal cord injury (Chopp, et al., *Neuroreport*, Vol. 11, pg. 3001 (2000); Wu, et al., *J. Neurosci. Res.*, Vol. 72, pg. 393 (2003)) and cardiac disorders (Tomita, et al., *Circulation*, Vol. 100, pg. 247 (1999). Shake, et al., *Ann. Thorac. Surg.*, Vol. 73, pg. 1919 (2002)). Importantly, promising results also have been reported in clinical trials for osteogenesis imperfecta (Horowitz, et al., *Blood*, Vol. 97, pg. 1227 (2001); Horowitz, et al. *Proc. Nat. Acad. Sci.*, Vol. 99, pg. 8932 (2002)) and enhanced engraftment of heterologous bone marrow transplants (Frassoni, et al., *Int. Society for Cell Therapy*, SA006 (abstract) (2002); Koc, et al., *J. Clin. Oncol.*, Vol. 18, pgs. 307-316 (2000)).

In addition, in vitro studies from different laboratories have shown that MSCs can inhibit T-cell proliferation either in mixed lymphocyte cultures or by other stimuli such as antigens and mitogens (Di Nicola, et al., *Blood*. Vol. 99, pgs. 3638-3843 (2002); Tse, et al., *Transplantation*, Vol. 75, pgs. 389-397 (2003); Aggarwal, et al., *Blood*, Vol. 105, pgs. 1815-1822 (2005)). Recent in vitro data demonstrate further that MSCs decrease the secretion of pro-inflammatory cytokines, tumor necrosis factor-α (TNF-α), and Interferon-γ (IFN-γ), and simultaneously increase production of anti-inflammatory cytokines Interleukin-10 (IL-10) and Interleukin-4 (IL-4) by immune cells. (Aggarwal, 2005). These results indicate that due to immunomodulatory and anti-inflammatory activities, MSCs can be beneficial for treatment of immunological responses which occur in graft-versus-host disease (GVHD), solid organ transplantation, and autoimmune diseases such as multiple sclerosis and rheumatoid arthritis. A clinical case report demonstrating the therapeutic effect of MSCs for acute GVHD supports strongly this hypothesis. (Le Blanc, et al., *The Lancet*. Vol. 363, pgs. 1439-1441 (2004).)

The TNF-α receptors are expressed on the surface of mesenchymal stem cells. Accumulated data indicate that TNF-α is an important regulator of mesenchymal stem cell function. Incubation of TNF-α with human mesenchymal stem cells in culture upregulates prostaglandin E2 ($PGE_2$) and keratinocyte growth factor (KGF) secretion, induces indoleamine 2,3 deoxygenase (IDO) enzyme activity and stimulates cell migration. TNF-α has been shown to be present at wound and inflammatory sites, especially in organs targeted by graft-versus-host disease. (Koide, et al., *Transplantation*, Vol. 64, pgs. 518-524 (1997); Kuroiwa, et al., *J. Clin. Invest.*, Vol. 107, pgs. 1365-1373 (2001); Deans, et al., *Exp. Hematol.*, Vol. 28, pgs. 875-884 (2002); Ellison, et al., *J. Clin. Immunol.*, Vol. 24, pgs. 197-211 (2004)). Thus, such data indicate that expression of TNF-α receptors by mesenchymal stem cells may be critical for immunosuppressive, immunomodulatory, anti-inflammatory, tissue-repairing, or wound-healing activities, as well as migration to sites of inflammation.

There are two types of TNF-α receptors, or TNFRs: Type I (TNFRI), also known as p55, and Type II (TNFRII), also known as p75. (Tartaglia, et al., *Proc. Nat. Acad. Sci*, Vol. 88, pgs. 9292-9296 (1991).) Both types of TNF-α receptors are present on MSCs; however, TNFRI is the predominant type. (Vancheri, et al., *Am. J. Respir. Cell Mol. Biol.*, Vol. 22, pgs. 628-634 (2000): Debets, et al., *Cytokine*, Vol. 8, pgs. 80-88 (1996).)

BRIEF DESCRIPTION OF SEVERAL VIEWS OF THE DRAWINGS

The invention now will be described with respect to the drawings wherein.

DETAILED DESCRIPTION OF THE INVENTION

In accordance with an aspect of the present invention, there is provided a composition comprising mesenchymal stem cells. The mesenchymal stem cells express the TNF-α receptor Type I (TNFR1) in a varying amount effective to inhibit the proliferation of lymphocytes. In one embodiment, the mesenchymal stem cells express TNFRI in an amount of at least 13 pg/$10^6$ cells. In another embodiment, the mesenchymal stem cells express TNFRI in an amount, for example, of at least 15 pg/$10^6$ cells. In yet another embodiment, the mesenchymal stem cells express TNFRI in an amount of at least 18 pg/$10^6$ cells.

Although the scope of the present invention is not to be limited to any theoretical reasoning, Applicants have found that mesenchymal stem cells which express the TNF-α receptor Type I in an amount from, for example, at least 13 pg/$10^6$ cells inhibit the proliferation of lymphocytes. Such mesenchymal stem cells are particularly useful in inhibiting immune responses, and more particularly such mesenchymal stem cells are useful in the treatment of graft-versus-host disease; solid organ transplant rejection such as, for example, heart transplant rejection, liver transplant rejection, pancreas transplant rejection, intestine transplant rejection, and kidney transplant rejection; and autoimmune diseases such as, for example, rheumatoid arthritis, multiple sclerosis, Type I diabetes, Crohn's disease, Guillain-Barré syndrome, lupus erythematosus, myasthenia gravis, optic neuritis, psoriasis, Graves' disease, Hashimoto's disease, Ord's thyroiditis, aplastic anemia, Reiter's syndrome, autoimmune hepatitis, primary biliary cirrhosis, antiphospholipid antibody syndrome, opsoclonus myoclonus syndrome, temporal arteritis, acute disseminated encephalomyelitis, Goodpasture's syndrome, Wegener's granulomatosis, coeliac disease, pemphigus, polyarthritis, warm autoimmune hemolytic anemia, and scleroderma.

In one embodiment, the mesenchymal stem cells are obtained from a mammal. The mammal may be a primate, including human and non-human primates.

The mesenchymal stem cells may be a homogeneous composition or may be a mixed cell population enriched in MSCs. Homogeneous mesenchymal stem cell compositions may be obtained by culturing adherent marrow or periosteal cells, and the mesenchymal stem cells may be identified by specific cell surface markers which are identified with unique monoclonal antibodies. A method for obtaining a cell population enriched in mesenchymal stem cells is described, for example, in U.S. Pat. No. 5,486,359. Alternative sources for mesenchymal stem cells include, but are not limited to, blood, skin, cord blood, muscle, fat, bone, and perichondrium.

The varying amount, but at least 13 pg/$10^6$ cells, of cellular TNF-α receptor, such as TNF-α receptor Type I, that is expressed in a culture of mesenchymal stem cells may be determined by methods known to those skilled in the art. Such methods include, but are not limited to, quantitative assays such as quantitative ELISA assays, for example. It is to be understood, however, that the scope of the present invention is not to be limited to any particular method for determining the amount of TNF-α receptor and it should be appreciated that the amount of expression can vary.

In one embodiment, the amount of TNF-α receptor expressed by a culture of mesenchymal stem cells is determined by an ELISA assay. In such an assay, a cell lysate from a culture of mesenchymal stem cells is added to a well of an ELISA plate. The well may be coated with an antibody, either a monoclonal or a polyclonal antibody(ies), against the TNF-α receptor. The well then is washed, and then contacted with an antibody, either a monoclonal or a polyclonal antibody(ies), against the TNF-α receptor. The antibody is conjugated to an appropriate enzyme, such as horseradish peroxidase, for example. The well then may be incubated, and then is washed after the incubation period. The wells then are contacted with an appropriate substrate, such as one or more chromogens. Chromogens which may be employed include, but are not limited to, hydrogen peroxide and tetramethylbenzidine. After the substrate(s) is (are) added, the well is incubated for an appropriate period of time.

Upon completion of the incubation, a "stop" solution is added to the well in order to stop the reaction of the enzyme with the substrate(s). The optical density (OD) of the sample then is measured. The optical density of the sample is correlated to the optical densities of samples containing known amounts of TNF-α receptor in order to determine the amount of TNF-α receptor expressed by the culture of mesenchymal stem cells being tested.

Thus, the present invention provides for the selection of a population of mesenchymal stem cells which express TNF-α receptor Type 1 in an amount, for example, of at least 13 pg/$10^6$ cells. However, it should be appreciated by those skilled in the art that the selected population of mesenchymal stem cells of the present invention express the desired amount of TNF-α receptor Type 1 while other populations may not express the desired amount of receptor due to the biological nature of the present invention. It is believed, for example, that approximately 98% of the selected mesenchymal stem cell population of the present invention express the desired TNF-α receptor Type 1 level while the remaining portion of that population may not. Such selected mesenchymal stem cells then may be admixed with an appropriate pharmaceutical carrier for treatment of the diseases and disorders mentioned hereinabove. For example, the mesenchymal stem cells may be administered as a cell suspension including a pharmaceutically acceptable liquid medium for injection.

The mesenchymal stem cells of the present invention are administered to an animal in an amount effective to treat one or more of the above-mentioned diseases or disorders in the animal. The animal may be a mammal, and the mammal may be a primate, including human and non-human primates. The mesenchymal stem cells may be administered systemically, such as, for example, by intravenous, intraarterial, or intraperitoneal administration. The exact dosage of mesenchymal stem cells to be administered is dependent upon a variety of factors, including, but not limited to, the age, weight, and sex of the patient, the disease(s) or disorder(s) being treated, and the extent and severity thereof.

The invention now will be described with respect to the following examples; however, the scope of the present invention is not intended to be limited thereby.

EXAMPLE 1

In order to investigate the role of TNFRI on the immunosuppressive hMSC activity, hMSCs were transfected transiently by antisense TNFRI type oligonucleotides with the purpose to decrease TNFRI expression (Shen et al., *J. Biol. Chem.*, Vol. 272, pgs. 3550-3553 (1997)). In order to reach different degrees of TNFRI expression inhibition, three different concentrations of oligonucleotides were used for transfection experiments. Non-transfected MSCs and MSCs transfected with a sense oligonucleotide were used as controls. TNFRI expression on hMSCs was analyzed in cell lysates by ELISA, and effect of reduction in TNFRI expression on hMSC capacity to inhibit hPBMC proliferation in vitro was investigated.

Human bone marrow-derived MSCs at Passage 5 from 7 different donors were used for analysis. Cells were obtained from bone marrow aspirates, and isolated using hespan. The cells then were cultured through Passage 5, and frozen in a standard cryopreservation solution containing 5% human serum albumin (HSA) and 10% dimethylsulfoxide in Plasmalyte A. (Baxter) The cells were stored at $-80°$ C. prior to analysis. On the day of the experiment, the hMSCs were thawed, counted, and plated into 6-well tissue culture plates at $2.5 \times 10^5$ cells/well. After overnight incubation, cells were transfected with TNFRI sense or antisense oligonucleotides at concentrations of 1.25, 2.5 and 5 μg/mL according to the transfection reagent manufacturer's protocol (Invitrogen, the Cellfectin transfection reagent product insert). At 24 hours post-transfection, the cells were collected from the plates. One group of cells was lysed, and expression of TNFRI in cell lysates was analyzed by ELISA according to the sTNFRI ELISA protocol (R&D Systems, product insert). TNFRI expression was expressed in pg of receptor per $1 \times 10^6$ cells.

For the ELISA assay. $2.5 \times 10^5$ MSCs per well were lysed directly in wells using 250 μl/well of Cell Lytic-mammalian cell lysis/extraction reagent (Sigma, Catalog No. 0-2978) containing a complete protein inhibitor cocktail (Roche). The cell lysates then were centrifuged for 10 minutes at 12,000-14,000 rpm in an Eppendorf centrifuge to remove insoluble material from the lysis buffer solution. The cell lysates then were collected in a new tube for use in the ELISA assay.

An alternative method of cell lysis, i.e., lysis of cell pellets in tubes, also was carried out for frozen cells and for cells collected from tissue culture plates or flasks. Both methods, direct cell lysis in culture plates and lysis of cell pellets in tubes, gave comparable results.

A commercially available ELISA kit, Quantikine®, Human sTNFRI (Catalog No. DRT 100, R&D Systems) was used for the detection of TNFRI in cell lysates. This assay provides for the measurement of both soluble as well as cell-associated TNFRI (Qjwang, et al., *Biochemistry*, Vol. 36, pg. 6033 (1997).) The assay employs the quantitative sandwich enzyme immunoassay technique. The assay employs a microplate that includes wells that have been pre-coated with a monoclonal antibody specific for TNFRI. TNFRI present in calibrator samples, quality control samples, or samples of MSC cell lysates is captured by the immobilized TNFRI antibody. After washing away any unbound substances, enzyme-linked polyclonal antibodies specific for TNFRI is added to the wells. Following a wash step to remove any unbound enzyme-linked antibody, a substrate solution was added to the wells, and color develops in proportion to the amount of bound TNFRI. The color development then is stopped, and the intensity of the color is measured using an ELISA reader.

The details of the ELISA are given hereinbelow.

500 of assay diluent HD1-7, a buffered protein base with preservative, were added to the wells of an ELISA plate. The wells were coated with a monoclonal antibody specific for TNFRI. 200 μl of either calibrator samples (containing 500 pg/ml, 250 pg/ml, 125 pg/ml, 62.5 pg/ml, 31.25 pg/ml, 15.625 pg/ml, or 7.813 pg/ml of soluble human TNFRI), quality control samples (containing 45 pg/ml, 100 pg/ml, or 250 pg/ml of human TNFRI), or cell lysates then were added to the wells. Prior to the addition of the calibration and quality control sample to the wells, such samples were treated with the Cell Lytic-mammalian cell lysis extraction agent (Sigma) and complete protein inhibitor cocktail (Roche) as hereinabove described. The plate then was covered with an adhesive strip, and incubated for 2 hours±10 minutes at room temperature.

The liquid then was decanted from each well by inverting the plate over a sink, and then the plate was washed three times. The plate is washed each time with 400 μl of a wash buffer added to each well. Residual liquid was removed by inverting the plate and blotting.

200 μl of soluble TNFRI polyclonal antibodies conjugated to horseradish peroxidase then were added to each well. The plate then was incubated for 2 hours±10 minutes at room temperature. The liquid then was decanted from each well, and each well was washed three times with 400 μl of wash buffer as hereinabove described.

200 μl of a substrate solution of stabilized hydrogen peroxide and stabilized tetramethylbenzidine chromogen then were added to each well. The plate then was incubated for 20 minutes±10 minutes at room temperature in the dark. 50 μl of a solution of 2N sulfuric acid then were added to each well. The optical density (OD) of each sample then was measured within 30 minutes with a 450 nm test and a 570 nm reference filter. The optical density values then were correlated to the amounts of TNFRI in the cell lysate samples.

Quantitation was achieved by comparing the signal from samples of MSC cell lysates to TNFRI standards assayed at the same time. Each ELISA run provided a calibration curve and included duplicate quality control samples plated in front and after test samples. Quality control samples were used for ELISA run validity assessment. TNFRI expression data were expressed in picograms of receptor per $1 \times 10^6$ cells. The raw data (in pg/ml) reflect TNFRI in picograms per $1 \times 10^6$ cells ($2.5 \times 10^5$ cells were lysed in 250 μl of the lysis reagent, thus corresponding to $1 \times 10^6$ cells/ml).

The ELISA values for the calibration samples are given in Table 1 below.

TABLE 1

Calculations for ELISA run calibration standards

| Calibrator Sample | Theoretical Concentration of Calibrations (pg/mL) | OD* Values | OD Mean Value | Standard Deviation | Back Calculated Concentration for Standards (pg/mL) | Calculated Mean Concentration for Standards (pg/mL) | % DFT* | % CV* |
|---|---|---|---|---|---|---|---|---|
| St01 | 500 | 2.431 2.443 | 2.437 | 0.008 | 498.003 501.842 | 499.923 | −0.015 | 0.3 |

TABLE 1-continued

Calculations for ELISA run calibration standards

| Calibrator Sample | Theoretical Concentration of Calibrations (pg/mL) | OD* Values | OD Mean Value | Standard Deviation | Back Calculated Concentration for Standards (pg/mL) | Calculated Mean Concentration for Standards (pg/mL) | % DFT* | % CV* |
|---|---|---|---|---|---|---|---|---|
| St02 | 250 | 1.487 | 1.476 | 0.016 | 252.746 | 250.306 | 0.123 | 1.1 |
|  |  | 1.464 |  |  | 247.867 |  |  |  |
| St03 | 125 | 0.804 | 0.815 | 0.015 | 122.64 | 124.447 | −0.442 | 1.8 |
|  |  | 0.825 |  |  | 126.255 |  |  |  |
| St04 | 62.5 | 0.453 | 0.442 | 0.016 | 64.774 | 63.024 | 0.839 | 3.5 |
|  |  | 0.431 |  |  | 61.274 |  |  |  |
| St05 | 31.25 | 0.25 | 0.239 | 0.016 | 32.749 | 30.939 | −0.996 | 6.8 |
|  |  | 0.227 |  |  | 29.128 |  |  |  |
| St06 | 15.625 | 0.143 | 0.145 | 0.002 | 15.765 | 16.007 | 2.446 | 1.5 |
|  |  | 0.146 |  |  | 16.249 |  |  |  |
| St07 | 7.813 | 0.092 | 0.093 | 0.001 | 7.368 | 7.537 | −3.528 | 1.5 |
|  |  | 0.094 |  |  | 7.706 |  |  |  |

*Note:
OD—optical density;
% DFT—% Difference from Theoretical;
CV %—% Coefficient of Variance The ELISA values for the quality control samples are given in Table 2 below.

TABLE 2

Calculations for ELISA run Quality Control (QC) samples

| QC Samples: | Theoretical Concentrations for QCs (pg/mL) | OD* Values | OD Mean Value | Standard Deviation | Back Calculated Concentration for QCs (pg/mL) | Calculated Mean Concentration for QCs (pg/mL) | % DFT* | % CV* |
|---|---|---|---|---|---|---|---|---|
| Front QCs |  |  |  |  |  |  |  |  |
| QC01 | 45 | 0.366 | 0.372 | 0.008 | 50.991 | 51.938 | 15.417 | 2.3 |
|  |  | 0.378 |  |  | 52.884 |  |  |  |
| QC02 | 100 | 0.753 | 0.733 | 0.028 | 113.944 | 110.572 | 10.572 | 3.9 |
|  |  | 0.713 |  |  | 107.2 |  |  |  |
| QC03 | 250 | 1.503 | 1.509 | 0.008 | 256.165 | 257.454 | 2.982 | 0.6 |
|  |  | 1.515 |  |  | 258.742 |  |  |  |
| Back QCs |  |  |  |  |  |  |  |  |
| QC01 | 45 | 0.315 | 0.332 | 0.024 | 42.964 | 45.638 | 1.418 | 7.2 |
|  |  | 0.349 |  |  | 48.312 |  |  |  |
| QC02 | 100 | 0.712 | 0.698 | 0.021 | 107.033 | 104.609 | 4.609 | 2.9 |
|  |  | 0.683 |  |  | 102.185 |  |  |  |
| QC03 | 250 | 1.547 | 1.558 | 0.015 | 265.671 | 267.967 | 7.187 | 1 |
|  |  | 1.568 |  |  | 270.263 |  |  |  |

*Note:
OD—optical density;
% DFT—% Difference from Theoretical;
CV %—% Coefficient of Variance Based on the ELISA values for the calibration and quality control samples shown in Tables 1 and 2 hereinabove, TNFRI expression in pg per $1\times10^6$ cells for samples of mesenchymal stem cells from the donors was determined.

As described hereinabove, the mesenchymal stem cells from each donor were non-transfected, or transfected with a TNFRI sense or antisense oligonucleotide at a concentration of 1.25, 2.5, or 5 µg/ml. The ELISA values and the amount of TNFRI expressed by each of the mesenchymal stem cell samples from each of the donors are given in Table 3 below.

TABLE 3

Calculations for ELISA run test samples

| hMSC Donor # | Sample description: | OD* Values | OD Mean Value | SD* | Calculated Concentration (pg/mL) | Mean Concentration (pg/mL) | TNFRI in pg per 1 × 10$^6$ cells | % CV* |
|---|---|---|---|---|---|---|---|---|
| 24 | Control (non-transfected cells) | 0.385 0.383 | 0.384 | 0.001 | 53.989 53.674 | 53.831 | 53.831 | 0.4 |
| | Control oligo-transfected cells 5 ug/mL | 0.278 0.253 | 0.266 | 0.018 | 37.15 33.221 | 35.186 | 35.186 | 6.7 |
| | Control oligo-transfected cells 2.5 µg/mL | 0.348 0.356 | 0.352 | 0.006 | 48.155 49.415 | 48.785 | 48.785 | 1.6 |
| | Control oligo-transfected cells 1.25 µg/mL | 0.386 0.369 | 0.378 | 0.012 | 54.147 51.464 | 52.806 | 52.806 | 3.2 |
| | TNFRI anti-sense oligo-transfected cells 5 µg/mL | 0.117 0.108 | 0.113 | 0.006 | 11.533 10.047 | 10.79 | 10.79 | 5.7 |
| | TNFRI anti-sense oligo-transfected cells 2.5 µg/mL | 0.254 0.236 | 0.245 | 0.013 | 33.378 30.546 | 31.962 | 31.962 | 5.2 |
| | TNFRI anti-sense oligo-transfected cells 1.25 | 0.321 0.3 | 0.311 | 0.015 | 43.907 40.607 | 42.257 | 42.257 | 4.8 |
| 007 | Control (non-transfected cells) | 0.368 0.365 | 0.367 | 0.002 | 51.306 50.833 | 51.07 | 51.07 | 0.6 |
| | Control oligo-transfected cells 5 µg/mL | 0.226 0.212 | 0.219 | 0.01 | 28.97 26.761 | 27.866 | 27.866 | 4.5 |
| | Control oligo-transfected cells 2.5 µg/mL | 0.293 0.25 | 0.272 | 0.03 | 39.507 32.749 | 36.128 | 36.128 | 11.2 |
| | Control oligo-transfected cells 1.25 µg/mL | 0.308 0.263 | 0.286 | 0.032 | 41.864 34.793 | 38.329 | 38.329 | 11.1 |
| | TNFRI anti-sense oligo-transfected cells 5 µg/mL | 0.123 0.104 | 0.114 | 0.013 | 12.517 9.382 | 10.949 | 10.949 | 11.8 |
| | TNFRI anti-sense oligo-transfected cells 2.5 µg/mL | 0.269 0.216 | 0.243 | 0.037 | 35.736 27.393 | 31.565 | 31.565 | 15.5 |
| | TNFRI anti-sense oligo-transfected cells 1.25 µg/mL | 0.313 0.293 | 0.303 | 0.014 | 42.65 39.507 | 41.078 | 41.078 | 4.7 |
| 014 | Control (non-transfected cells) | 0.377 0.383 | 0.38 | 0.004 | 52.726 53.674 | 53.2 | 53.2 | 1.1 |
| | Control oligo-transfected cells 5 µg/mL | 0.251 0.247 | 0.249 | 0.003 | 32.907 32.277 | 32.592 | 32.592 | 1.1 |
| | Control oligo-transfected cells 2.5 µg/mL | 0.338 0.291 | 0.315 | 0.033 | 46.581 39.193 | 42.887 | 42.887 | 10.6 |
| | Control oligo-transfected cells 1.25 µg/mL | 0.356 0.337 | 0.347 | 0.013 | 49.415 46.424 | 47.919 | 47.919 | 3.9 |
| | TNFRI anti-sense oligo-transfected cells 5 µg/mL | 0.11 0.098 | 0.104 | 0.008 | 10.378 8.379 | 9.379 | 9.379 | 8.2 |

TABLE 3-continued

Calculations for ELISA run test samples

| hMSC Donor # | Sample description: | OD* Values | OD Mean Value | SD* | Calculated Concentration (pg/mL) | Mean Concentration (pg/mL) | TNFRI in pg per 1 × 10⁶ cells | % CV* |
|---|---|---|---|---|---|---|---|---|
| | TNFRI antisense oligo-transfected cells 2.5 µg/mL | 0.211 0.2 | 0.206 | 0.008 | 26.603 24.864 | 25.733 | 25.733 | 3.8 |
| | TNFRI antisense oligo-transfected cells 1.25 µg/mL | 0.3 0.288 | 0.294 | 0.008 | 40.607 38.722 | 39.664 | 39.664 | 2.9 |
| 015 | Control (non-transfected cells) | 0.475 0.462 | 0.469 | 0.009 | 68.284 66.209 | 67.246 | 67.246 | 2 |
| | Control oligo-transfected cells 5 µg/mL | 0.278 0.28 | 0.279 | 0.001 | 37.15 37.465 | 37.308 | 37.308 | 0.5 |
| | Control oligo-transfected cells 2.5 µg/mL | 0.34 0.345 | 0.343 | 0.004 | 46.896 47.683 | 47.289 | 47.289 | 1 |
| | Control oligo-transfected cells 1.25 µg/mL | 0.419 0.406 | 0.413 | 0.009 | 59.37 57.31 | 58.34 | 58.34 | 2.2 |
| | TNFRI antisense oligo-transfected cells 5 µg/mL | 0.13 0.12 | 0.125 | 0.007 | 13.658 12.025 | 12.842 | 12.842 | 5.7 |
| | TNFRI antisense oligo-transfected cells 2.5 µg/mL | 0.253 0.27 | 0.262 | 0.012 | 33.221 35.893 | 34.557 | 34.557 | 4.6 |
| | TNFRI antisense oligo-transfected cells 1.25 µg/mL | 0.377 0.384 | 0.381 | 0.005 | 52.726 53.831 | 53.279 | 53.279 | 1.3 |
| 23 | Control (non-transfected cells) | 0.260 0.249 | 0.255 | 0.008 | 40.591 38.672 | 39.632 | 39.632 | 3.1 |
| | Control oligo-transfected cells 5 µg/mL | 0.191 0.177 | 0.184 | 0.010 | 28.560 26.117 | 27.339 | 27.339 | 5.4 |
| | Control oligo-transfected cells 2.5 µg/mL | 0.216 0.203 | 0.209 | 0.009 | 32.919 30.653 | 31.786 | 31.786 | 4.4 |
| | Control oligo-transfected cells 1.25 µg/mL | 0.222 0.222 | 0.222 | 0.000 | 33.965 33.965 | 33.965 | 33.965 | 0.0 |
| | TNFRI antisense oligo-transfected cells 5 µg/mL | 0.107 0.105 | 0.106 | 0.001 | 13.798 13.441 | 13.620 | 13.620 | 1.3 |
| | TNFRI antisense oligo-transfected cells 2.5 µg/mL | 0.206 0.168 | 0.187 | 0.027 | 31.176 24.544 | 27.860 | 27.860 | 14.4 |
| | TNFRI antisense oligo-transfected cells 1.25 µg/mL | 0.213 0.211 | 0.212 | 0.001 | 32.396 32.048 | 32.222 | 32.222 | 0.7 |
| 486 | Control (non-transfected cells) | 0.249 0.248 | 0.249 | 0.001 | 41.244 41.053 | 41.148 | 41.148 | 0.3 |
| | Control oligo-transfected cells 5 µg/mL | 0.149 0.123 | 0.136 | 0.018 | 22.401 17.560 | 19.981 | 19.981 | 13.5 |

TABLE 3-continued

Calculations for ELISA run test samples

| hMSC Donor # | Sample description: | OD* Values | OD Mean Value | SD* | Calculated Concentration (pg/mL) | Mean Concentration (pg/mL) | TNFRI in pg per $1 \times 10^6$ cells | % CV* |
|---|---|---|---|---|---|---|---|---|
|  | Control oligo-transfected cells 2.5 µg/mL | 0.246 0.215 | 0.231 | 0.022 | 40.672 34.792 | 37.732 | 37.732 | 9.5 |
|  | Control oligo-transfected cells 1.25 µg/mL | 0.263 0.242 | 0.253 | 0.015 | 43.915 39.911 | 41.913 | 41.913 | 5.9 |
|  | TNFRI anti-sense oligo-transfected cells 5 µg/mL | 0.071 0.065 | 0.068 | 0.004 | 7.917 6.805 | 7.361 | 7.361 | 6.2 |
|  | TNFRI anti-sense oligo-transfected cells 2.5 µg/mL | 0.142 0.142 | 0.142 | 0.000 | 21.096 21.096 | 21.096 | 21.096 | 0.0 |
|  | TNFRI anti-sense oligo-transfected cells 1.25 µg/mL | 0.193 0.164 | 0.179 | 0.021 | 30.644 25.204 | 27.924 | 27.924 | 11.5 |
| 13 | Control (non-transfected cells) | 0.211 0.207 | 0.209 | 0.003 | 34.037 33.282 | 33.659 | 33.658 | 1.4 |
|  | Control oligo-transfected cells 5 µg/mL | 0.134 0.133 | 0.134 | 0.01 | 19.606 19.420 | 19.513 | 19.513 | 0.5 |
|  | Control oligo-transfected cells 2.5 µg/mL | 0.195 0.180 | 0.188 | 0.011 | 31.020 28.201 | 29.611 | 29.611 | 5.7 |
|  | Control oligo-transfected cells 1.25 µg/mL | 0.207 0.176 | 0.192 | 0.022 | 33.282 27.451 | 30.366 | 38.329 | 11.4 |
|  | TNFRI anti-sense oligo-transfected cells 5 µg/mL | 0.087 0.073 | 0.080 | 0.010 | 10.882 8.288 | 9.585 | 9.585 | 12.4 |
|  | TNFRI anti-sense oligo-transfected cells 2.5 µg/mL | 0.156 0.113 | 0.135 | 0.030 | 23.708 15.703 | 19.706 | 19.706 | 22.6 |
|  | TNFRI anti-sense oligo-transfected cells 1.25 µg/mL | 0.208 0.140 | 0.174 | 0.048 | 33.470 20.723 | 27.097 | 27.097 | 27.6 |

*Note:
OD—optical density;
SD—Standard Deviation;
CV %—% Coefficient of Variance From the above data shown in Table 3, the mean TNFRI expression, in picograms per $1 \times 10^6$ cells, was determined for non-transfected (control) mesenchymal stem cells, as well as mesenchymal stem cells transfected with 1.25, 2.5, or 5 µl/ml of antisense or sense oligonucleotides. The mean TNFRI expression values are given in Table 4 below.

TABLE 4

TNFRI expression by hMSCs transfected with anti-sense and control (sense) oligonucleotides: summary for 7 tested hMSC donors

| hMSC donor #: | TNFRI expression in pg per 1 × 10⁶ cells | | | | | | | Mean for 7 Donors | SD |
|---|---|---|---|---|---|---|---|---|---|
| | 486 | 13 | 24 | 007 | 14 | 15 | 23 | | |
| Control (non-transfected cells | 41* | 34 | 54 | 51 | 53 | 67 | 40 | 48.57 | 11.09 |
| TNFRI anti-sense oligo-transfected cells 5 μg/mL | 7 | 10 | 11 | 11 | 9 | 13 | 14 | 10.71 | 2.36 |
| TNFRI anti-sense oligo-transfected cells 2.5 μg/mL | 21 | 20 | 32 | 32 | 26 | 35 | 28 | 27.71 | 5.74 |
| TNFRI anti-sense oligo-transfected cells 1.25 μg/mL | 28 | 27 | 42 | 41 | 40 | 53 | 32 | 37.57 | 9.22 |
| Control (sense) oligo-transfected cells 5 μg/mL | 20 | 20 | 35 | 28 | 33 | 37 | 27 | 28.57 | 6.85 |
| Control (sense) oligo-transfected cells 2.5 μg/mL | 38 | 30 | 49 | 36 | 43 | 47 | 32 | 39.29 | 7.30 |
| Control (sense) oligo-transfected cells 1.25 μg/mL | 42 | 30 | 53 | 38 | 48 | 58 | 34 | 43.29 | 10.21 |

*Note:
These values represent mean TNFRI numbers (from table 3, column 8: "TNFRI in pg per 1 × 10⁶ cells") rounded to whole numbers A second group of transfected cells was used for investigation of the effect of hMSCs on hPBMC proliferation in vitro. Human PBMCs from two different donors were used for this assay. PBMCs were isolated from leukopheresed blood using Ficoll-Paque gradient centrifugation according to the manufacturer's protocol (Amersham Biosciences, Ficoll-Paque Plus product insert). Cells were stored frozen at −80° C. in a medium including 90% FBS and 10% DMSO prior to analysis. On the day of the experiment hPBMCs were thawed, counted and plated into 96-well tissue culture plates at $1\times10^5$ cells/well together with hMSCs ($1\times10^4$ cells/well). A combination of anti-CD3 (1 μg/mL) and anti-CD28 (1 μg/mL) antibodies was used to stimulate lymphocyte proliferation that represents an in vitro model for immune cell activation characteristics of GVHD and rejection of allogeneic organs. (Trickett, et al., *J. Immunol. Methods*, Vol. 275, pgs. 251-255 (2003); Koulova, et al., *J. Exp. Med.*, Vol. 173, No. 3, pgs. 759-762 (1991); Foster, et al., *Transplantation*, Vol. 76, No. 6; Czitrom, *Clin. Ortho. Relat. Res.*, Vol. 326, pgs. 11-24 (1996)). The plates then were incubated in a humidified atmosphere containing 5% $CO_2$. The proliferation of PBMCs alone and in the presence of MSCs was measured at day 5 from culture initiation by the addition of [Methyl-$^3$H]-thymidine at 1 μCi/well for the final 18-20 hrs of culture. After labeling, the cells were transferred onto a glass filter using a 96-well plate harvester, and radioactivity incorporated into DNA was measured by a liquid scintillation beta-counter. The uptake of [Methyl-$^3$H]-thymidine into DNA in counts per minute (cpm) represents hPBMC proliferation. Final results were expressed as % inhibition of PBMC proliferation in the presence of MSCs calculated as:

100%−[Proliferation(PBMC+MSC,cpm)×100/Profiteration(PBMC,cpm)]

The results for the mesenchymal stem cells from each of the donors are given in Table 5 below.

TABLE 5

Inhibition of CD3/CD28-induced hPBMC proliferation by hMSCs transfected with anti-sense and control (sense) oligonucleotides: summary for 7 tested hMSC donors

| | % inhibition of hPBMC proliferation by hMSCs | | | | | | | | | | | |
|---|---|---|---|---|---|---|---|---|---|---|---|---|
| | hMSC donor #: | | | | | | | | | | | |
| | 486 | | 13 | | 24 | 007 | 14 | 15 | | 23 | | |
| hPBMC donor #: | 2 | 3 | 2 | 3 | 3 | 3 | 3 | 2 | 2 | 3 | Mean % for 7 donors | SD |
| Control (non-transfected cells) | 65 | 73 | 82 | 94 | 70 | 66 | 82 | 62 | 68 | 91 | 75.30 | 11.26 |
| TNFRI anti-sense oligo-transfected cells 5 μg/mL | 40 | 45 | 46 | 68 | 32 | 10 | 39 | 19 | 38 | 52 | 38.90 | 16.29 |

TABLE 5-continued

Inhibition of CD3/CD28-induced hPBMC proliferation by hMSCs
transfected with anti-sense and control (sense) oligonucleotides: summary for
7 tested hMSC donors

| | % inhibition of hPBMC proliferation by hMSCs | | | | | | | | | | |
|---|---|---|---|---|---|---|---|---|---|---|---|
| | hMSC donor #: | | | | | | | | | | |
| | 486 | 13 | 24 | 007 | 14 | 15 | 23 | | | Mean % | |
| hPBMC donor #: | 2 | 3 | 2 | 3 | 3 | 3 | 3 | 2 | 2 | 3 | for 7 donors | SD |
| TNFRI anti-sense oligo-transfected cells 2.5 µg/mL | 83 | 90 | 59 | 86 | ND | 73 | ND | 63 | 47 | 58 | 69.88 | 15.48 |
| TNFRI anti-sense oligo-transfected cells 1.25 µg/mL | 62 | 74 | 86 | ND | 72 | 64 | 57 | ND | 72 | 80 | 70.88 | 9.58 |
| Control (sense) oligo-transfected cells 5 µg/mL | 38 | 87 | 60 | 77 | 58 | 77 | 62 | 44 | 52 | 53 | 60.80 | 15.50 |
| Control (sense) oligo-transfected cells 2.5 µg/mL | 60 | 91 | 67 | ND | ND | 62 | 66 | 57 | 70 | 95 | 71.00 | 14.22 |
| Control (sense) oligo-transfected cells 1.25 µg/mL | 87 | ND | 68 | 71 | 66 | 68 | 36 | ND | 49 | 85 | 70.57 | 12.77 |

Note:
ND—no data

The above data with respect to inhibition of CD3/CD28 induced PBMC proliferation were correlated to the mean TNFRI expression data shown in Table 4 hereinabove. The correlated data with respect to mean TNFRI expression and inhibition of CD3/CD28 induced PBMC proliferation are given in Table 6 below.

TABLE 6

TNFRI expression and effect on hPBMC proliferation in
vitro by hMSCs transfected with TNFRI oligonucleotides

| Human MSCs condition | Oligonucleotide concentration (pg/mL) | % inhibition of hPBMC proliferation (Mean ± SD) | TNFRI Expression in pg/1 × 10⁶ MSCs (Mean ± SD) |
|---|---|---|---|
| Untransfected (Control MSCs) | Not applicable | 75.30 ± 11.26 | 48.57 ± 11.09 |
| Antisense oligonucleotide | 1.25 | 70.88 ± 9.58 | 37.57 ± 9.22 |
| | 2.5 | 69.88 ± 15.48 | 27.71 ± 5.74 |
| | 5 | 38.90 ± 16.29 | 10.71 ± 2.36 |
| Sense oligonucleotide (control oligonucleotide) | 1.25 | 70.57 ± 12.77 | 43.29 ± 10.21 |
| | 2.5 | 71.00 ± 14.22 | 39.29 ± 7.30 |
| | 5 | 60.80 ± 15.50 | 28.57 ± 6.85 |

Figure 1:
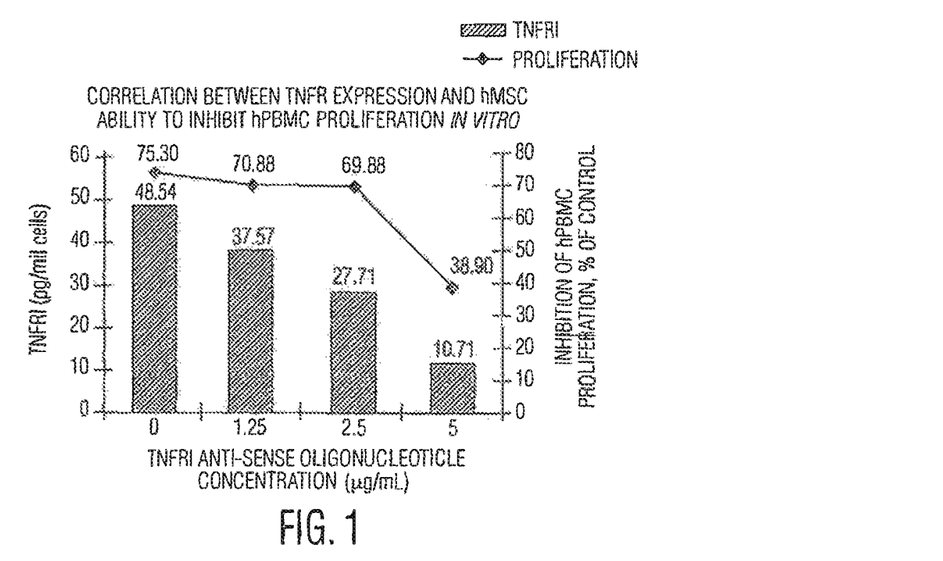
FIG. 1 is a graph of the correlation between TNFRI expression and the ability of MSCs to inhibit PBMC proliferation in vitro.

The results from these experiments show that hMSCs with decreased expression of TNFR type I (TNFRI) lose their ability to suppress hPBMC proliferation in vitro. The data support the premise that the expression of TNFRI is an essential link to the suppression of PBMC proliferation by MSCs. Thus, TNFRI can be used as a potency marker for MSC immunomodulative activity. Based on the obtained data, a potency threshold of 13.07 pg of, for example, TNFRI (mean±SD) per 1×10⁶ cells correlates with less than 50% inhibition of hPBMC proliferation (Table 6, FIG. 1). Thus, the present invention illustrates that those non-potent MSCs of a selected MSC population of at least one embodiment of the present invention are those cells expressing less than 13 pg TNFRI per 1×10⁶ cells.

EXAMPLE 2

TNFRI is a Temperature-Sensitive Marker of hMSC Functionality

Ex vivo handling of mammalian cells is restricted by a number of factors including temperature. For example, low temperatures such as −80±5° C., or lower, even as low as −135° C. or below (liquid nitrogen) are required for cell storage whereas ex vivo cell expansion requires a temperature of 37±0.5° C. Cell exposure to temperatures outside of the optimal ranges may lead to a decrease in cell functionality or cell death. Mammalian cells are able to withstand short-term minor temperature fluctuations; however, each type of cells has its own temperature tolerance range for cell culture maintenance, shipping, and storage.

As discussed herein, it is believed that the expression level of TNFRI on some hMSCs of the selected population of the present invention correlates with hMSC immunosuppressive activity. For example, the level of TNFRI expression by some of those hMSCs of less than 13 pg/10⁶ cells has been determined as a threshold, below which hMSCs begin to lose their ability to suppress an immune response (See FIG. 1). Thus, TNFRI expression is a marker of hMSC immunosuppression, an activity that is believed essential for MSCs to be efficacious for treatment of immunological reactions taking place in GVHD, organ rejection, autoimmune diseases, and other diseases. Here, effects of temperature fluctuations during storage of frozen hMSCs as well as the effect of time of exposure of cells to room temperature on expression of TNFRI on hMSCs was investigated.

Effect of Store Temperature Fluctuations on TNFRI Expression and hMSC Immunosuppressive Potential The objective of these experiments was to investigate the ability of the selected hMSCs to retain their functional characteristics after an exposure to temperatures above −80°

Figure 2:
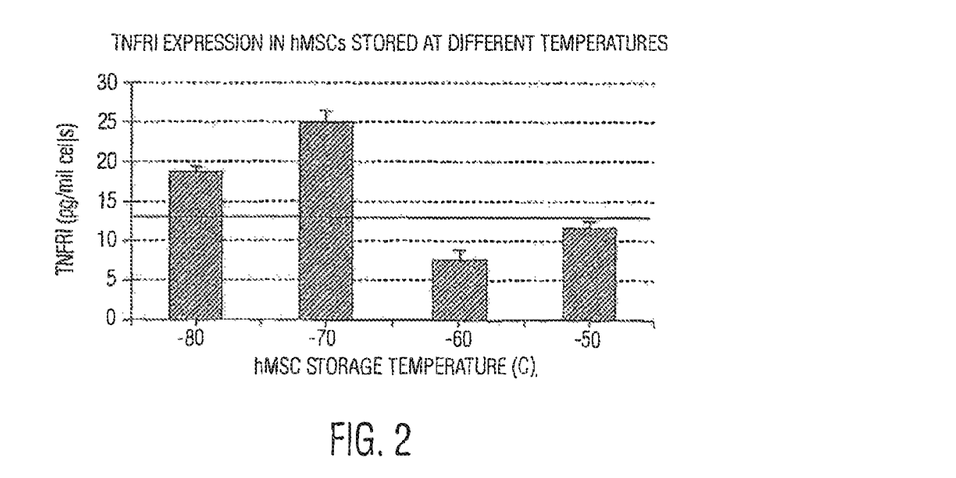
FIG. 2 is a graph showing varying TNFRI expression by human mesenchymal stem cells stored at −80° C., −70° C., −60° C., and −50° C.

C., which are not optimal temperatures for storage of frozen cells. Human MSCs were frozen at passage 5 and placed for storage in a freezer at −80±5° C. After several weeks, bags of frozen cells were removed from the −80±5° C. freezer and placed at either −70±5° C., −60±5° C., or −50±5° C. for 72±2 hours. After 72±2 hours, the bags were returned to storage at −80±5° C. for at least 24 hours before thaw and analysis. A set of bags moved from one −80±5° C. freezer to another, following the same schedule as the other bags, served as a control. On the day of the experiment the bags containing the cells were thawed, cells were counted, and cell lysates for the TNFRI ELISA were prepared as described in Example 1. The TNFRI ELISA was performed as described in Example 1. Results are summarized in FIG. 2 (bars show mean TNFRI values±SD for 3 hMSC bags). The data showed that exposure of hMSCs to temperatures of −60±5° C. or −50±5° C. decreases the TNFRI expression level: the level of TNFRI detected by ELISA was below the determined hMSC potency threshold of 13 pg/$10^6$ cells (represented by the solid line on the graph).

Figure 3:
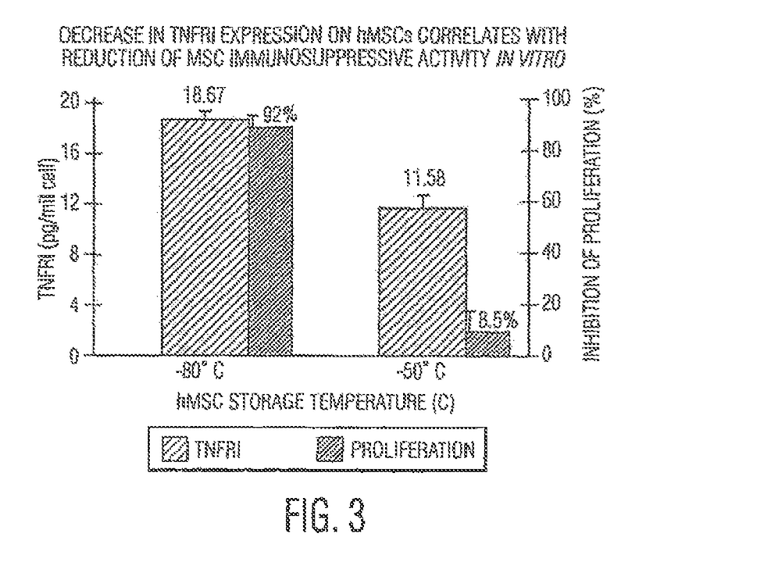
FIG. 3 is a graph showing TNFRI expression at varying levels and the correlating ability to inhibit PBMC proliferation in vitro. of human mesenchymal stem cells stored at −80° C. and −50° C.

Parallel with TNFRI measurement, two bags with hMSCs stored at −80±5° C. (optimal storage temperature served as a control) and at −50±5° C. (corresponding to a ±30° C. greater than the −80±5° C. optimal storage temperature) were used for investigation of hMSC immunosuppressive activity. The ability of the MSCs to suppress anti-CD3/CD28-induced proliferation of hPBMCs in vitro was evaluated as described in Example 1. The results showed that hMSCs stored at −50±5° C. lost their ability to suppress hPBMC proliferation, whereas cells stored at −80±5° C. inhibited hPBMC proliferation by 92%, but not up to 100% (FIG. 3, dark bars represent mean±SD % inhibition of hPBMC proliferation. Numbers inside the dark bars show numerical values). The immunosuppressive activity of MSCs is dependent on the level of TNFRI expression: for example, some cells expressing more than 13 pg/$10^6$ cells of TNFRI, which was determined as an MSC immunosuppressive potential threshold, are biologically active, while others cells with the TNFRI level below 13 pg/$10^6$ cells are not (FIG. 3, light bars represent mean±SD of the TNFRI expression level. Numbers inside the light bars show numerical values). Thus, non-optimal storage temperatures decrease TNFRI expression on hMSCs, and which correlates with decrease in hMSC functionality.

Effect of Cell Exposure Time to Room Temperature on TNFRI Expression on hMSC

Figure 4:
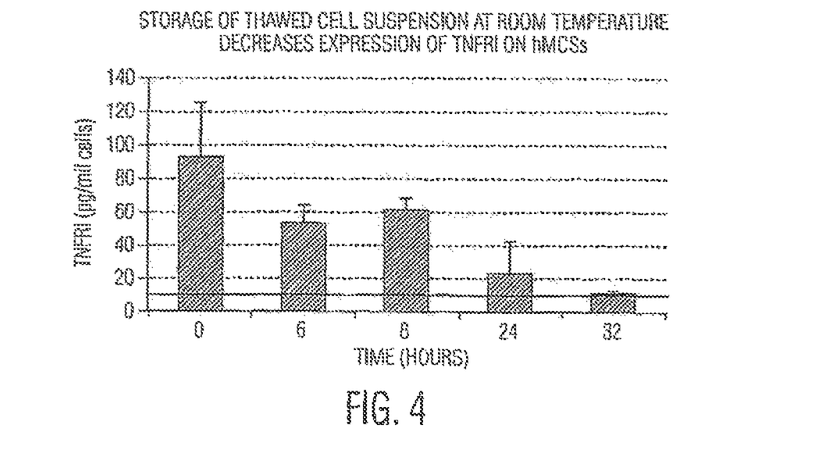
FIG. 4 is a graph showing TNFRI expression by human mesenchymal stem cells stored at −135° C. or below, and then thawed and kept at room temperature for 6, 8, 24, or 32 hours.

The results of this experiment serve as additional evidence that TNFRI expression on hMSCs is decreasing under cell exposure to non-optimal temperatures. In this experiment the effect of cell suspension storage at room temperature on TNFRI expression was studied. Two hMSC lots were used in the experiment. Bags containing hMSCs were stored at ≤−135° C. prior to the experiment. On the day of the experiment the cells were thawed and diluted with Plasmalyte A physiological solution (Baxter) in a manner that mimics the current cell processing for intravenous hMSC administration at clinical sites. The thawed and diluted hMSCs were kept at room temperature (22° C.-24° C.), and samples were taken and tested for the amount of TNFRI at 0 (immediately post-thaw—baseline), 6, 8, 10, 24, and 32 hours post-thawing. The results showed that exposure of hMSCs to room temperature decreased the TNFRI expression level on those hMSCs (FIG. 4, bars represent mean±SD of the TNFRI expression level for 2 hMSC lots. The solid line represents the TNFRI expression level of 13 pg/$10^6$ cells, which is the hMSC potency threshold). The significant decrease in TNFRI expression was observed at 24 hours and 32 hours, and it correlated with a significant decrease in cell viability (below 20%, data not shown).

Thus, the experiments described above show that TNFRI expression by hMSCs is sensitive to temperature, and TNFRI can be used as a marker of functionality of hMSC that were exposed to non-optimal temperatures during storage, shipping or cell processing.

The disclosures of all patents, publications, including published patent applications, depository accession numbers, and database accession numbers are hereby incorporated by reference to the same extent as if each patent, publication, depository accession number, and database accession number were specifically and individually incorporated by reference.

It is to be understood, however, that the scope of the present invention is not to be limited to the specific embodiments described above. The invention may be practiced other than as particularly described and still be within the scope of the accompanying claims.

The invention claimed is:

1. A method of treating a disease or disorder involving an activated immunological response in a human subject comprising,
   (i) determining the amount of cellular membrane-bound TNF-α receptor Type I expressed by at least one population of human mesenchymal stem cells;
   (ii) selecting a population of human mesenchymal stem cells that express cellular membrane-bound TNF-α receptor Type I in an amount of at least 27.7 pg/$10^6$ cells; and
   (iii) administering to the subject the selected population of mesenchymal stem cells.

2. The method of claim 1, wherein the population of mesenchymal stem cells express cellular membrane-bound TNF-α receptor Type I in an amount of at least 37.5 pg/$10^6$ cells.

3. The method of claim 1, wherein the population of mesenchymal stem cells express cellular membrane-bound TNF-α receptor Type I in an amount of at least 48.5 pg/$10^6$ cells.

4. The method of claim 1, wherein the activated immunological response is associated with an autoimmune disease.

5. The method of claim 4, where the autoimmune disease is selected from the group consisting of rheumatoid arthritis, multiple sclerosis, Type I diabetes, Crohn's disease, Guillain-Barré syndrome, lupus erythematosus, myasthenia gravis, optic neuritis, psoriasis, Graves' disease, Hashimoto's disease, Ord's thyroiditis, aplastic anemia, Reiter's syndrome, autoimmune hepatitis, primary biliary cirrhosis, antiphospholipid antibody syndrome, opsoclonus myoclonus syndrome, temporal arteritis, acute disseminated encephalomyelitis, Goodpasture's syndrome, Wegener's granulomatosis, coeliac disease, pemphigus, polyarthritis, warm autoimmune hemolytic anemia, and scleroderma.

6. The method of claim 1, wherein the activated immunological response is associated with graft versus host disease.

7. The method of claim 1, wherein the cellular membrane-bound TNF-α receptor Type I expression is determined using an enzyme-linked immunosorbent assay.

8. The method of claim 1, wherein the population of human mesenchymal stem cells was obtained from a human donor.

9. The method of claim 1, wherein the selected population of human mesenchymal stem cells is administered by intravenous, intraarterial, or intraperitoneal administration.

10. The method of claim 1, wherein the selected population of human mesenchymal stem cells has been frozen at −80° C. or below before administering to the subject.

11. The method of claim 1, wherein the population of human mesenchymal stem cells was obtained from a sample selected from the group consisting of adherent marrow, periosteal cells, blood, skin, cord blood, muscle, fat, bone, and perichondrium.

12. The method of claim 1, wherein the administering of the selected population of human mesenchymal stem cells to the human subject suppresses peripheral blood mononuclear cell (PBMC) proliferation.

13. The method of claim 12, wherein the PBMCs are CD3/CD28-induced PBMCs.

\* \* \* \* \*